United States Patent [19]

Schlaefer

[11] Patent Number: 5,101,073
[45] Date of Patent: Mar. 31, 1992

[54] PRODUCTION OF β-HYDROXYALKYLAMIDES

[75] Inventor: Francis W. Schlaefer, Penllyn, Pa.

[73] Assignee: Rohm and Haas Company, Philadelphia, Pa.

[21] Appl. No.: 573,524

[22] Filed: Aug. 27, 1990

[51] Int. Cl.$^5$ .......................... C07C 231/00
[52] U.S. Cl. ................... 564/137; 260/404; 260/404.5; 562/553; 562/554; 562/564; 564/134; 564/135; 564/136
[58] Field of Search ............... 564/135, 136, 137, 134; 260/404.5, 404; 560/155, 169; 562/553, 554, 564

[56] References Cited

U.S. PATENT DOCUMENTS

| | | | |
|---|---|---|---|
| 4,032,460 | 6/1977 | Zilch et al. | 252/8.55 B |
| 4,076,917 | 2/1978 | Swift et al. | 526/49 |
| 4,493,909 | 1/1985 | Haas et al. | 521/166 |
| 4,727,111 | 2/1988 | Pettit, Jr., et al. | 525/190 |

FOREIGN PATENT DOCUMENTS 2554443 5/1985 France.
0227844 12/1984 Japan.

OTHER PUBLICATIONS

Journal of Coatings Technology, 50 (643), 49-55 (1978).
Lomax et al., "B-Hydroxyalkylamides, etc.", *Journal of Coatings Technology*, 50 (643), 49-55 (1978).

*Primary Examiner*—Allen J. Robinson
*Assistant Examiner*—P. O'Sullivan
*Attorney, Agent, or Firm*—Lowell H. McCarter; T. P. Strobaugh

[57] ABSTRACT

A method of preparing solid hydroxyalkylamides by reacting carboxylic alkyl esters with alkanolamines at controlled reaction temperatures, removing the alcohol byproduct, controlling the temperature of the reaction mixture to form a slurry, maintaining the slurry and recovering the solid hydroxyalkylamides.

9 Claims, No Drawings

PRODUCTION OF β-HYDROXYALKYLAMIDES

BACKGROUND

1. Field of Invention

This invention relates to the production, purification, and isolation of hydroxyamides, which are useful as chemical intermediates and chemical crosslinkers.

2. Description of Prior Art

Hydroxyamides have been synthesized by the aminolysis of dimethyl esters by alkanolamines. Isolation and purification of solid hydroxyamide products is done conventionally either by recrystallization (*J. Coat. Tech.*, 50 (643), 49–55 (1978); U.S. Pat. Nos. 4,032,460; 4,076,917; 4,493,909; 4,727,111; Japanese Patent 56-062895) or by prilling/flaking. Using recrystallization, relatively pure product is obtained but product losses due to dissolution in the solvents used and the complexity of removing residual solvent from the product as well as recovering solvents for reuse pose significant disadvantages to this approach. Recrystallization is typically performed by dissolving the crude hydroxyamide in solvent, such as methanol/acetone, cooling to grow the crystals, filtering the product away from the mother liquors, and drying the product free of residual solvent. Alternatively, recrystallization may entail adding solvent to melted hydroxyamide, followed by crystal growth, filtration, and drying as described above.

Prilling/flaking requires that the hydroxyamide be maintained in a fluid state for several hours until the operation is complete. During this time in the molten state some of the product degrades to undesirable byproducts.

The physical state of the crude hydroxyamides of interest is that of a soft, sticky, waxy solid, which typically renders the materials unsuitable for use in powder coatings, such use requiring free-flowing powders. Certain hydroxyamides are useful as crosslinkers in powder coatings based on polyester or acrylate chemistries.

SUMMARY OF INVENTION

A process for producing solid hydroxyamides of the formula (I):

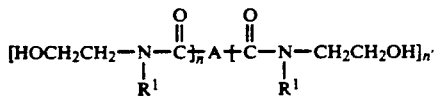

wherein A is a bond, a polyvalent organic radical or when n' is zero, A may be hydrogen or a monovalent organic radical selected from a saturated or unsaturated alkyl, aryl, carboxy lower alkenyl, lower alkoxycarbonyl lower alkenyl; $R^1$ is selected from the group consisting of hydrogen, lower alkyl, or hydroxy lower alkyl; n is an integer having a value of 1 to 10; and n' is an integer having a value of 0 to 2; which comprises reacting carboxylic alkyl esters with alkanolamines at a certain reaction temperature, removing the alcohol byproduct compound at atmospheric or reduced pressure, controlling the temperature of the crude reaction mixture until the hydroxyamide crystallizes to form a slurry, maintaining the slurry in the reaction mixture by temperature control (25° to 200° C., preferably 80° to 115° C.) for from about 15 minutes to about 12 hours (preferably 1 to 3 hours), followed by isolation of the hydroxyamide.

This invention involves a process for producing high purity solid hydroxyamides by first forming a slurry of the solid hydroxyamide in a liquid melt mixture of said hydroxyamide, amine precursors, and other minor process impurities, followed by flaking, prilling, casting, spray drying or other means of solidification to isolate the high purity solid hydroxyamide. In another aspect, this invention is used to produce solid hydroxyamides having the consistency of a free-flowing powder suitable for direct use as a crosslinker in powder coating formulations.

The invention may be practiced by cooling the crude mixture resulting from the base catalyzed aminolysis of a diester and an alkanolamine until a thick slurry develops. The temperature of the mixture is then varied to maintain slurry characteristics during the subsequent steps used for solidification (casting, prilling, flaking, and the like).

Solid hydroxyamides produced by this invention are superior to products produced by prior art methods of recrystallization in that physical form (free-flowing powder) characteristics equal or exceed that obtained from recrystallization and no solvents are involved, thus eliminating the additional steps of solvent removal/recovery. In contrast to prior art recrystallization methods (which "separates" impurities from the desired product), the invention uses the slurry environment (solid hydroxyamide in the presence of precursors and byproducts) to "convert" some of the byproduct impurities to the desired hydroxyamide product; the slurry conditions drive the chemical reaction towards completion. The invention may be used to produce hydroxyamides that are solids at room temperature, i.e., those having melting points above about 25° C. In comparison to the prior art methods of casting, prilling, or flaking, use of the invention results in an hydroxyamide product of much higher overall quality in that fewer impurities are present, since the process of the invention does not subject the hydroxyamides to long hold times at elevated temperatures in the molten state (non-slurry conditions) during which undesirable byproducts form. Also, the operations of filtration and drying, usually associated with recrystallization routes, are eliminated by use of the invention.

DETAILED DESCRIPTION OF INVENTION

Hydroxamides which may be produced by the process of the invention include those represented by formula I:

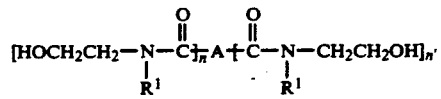

wherein A is a bond, a polyvalent organic radical or when n' is zero, A may be hydrogen or a monovalent organic radical where the organic radical is derived from a saturated or unsaturated alkyl radical wherein the alkyl radical contains from 1–60 carbon atoms, such as methyl, ethyl, propyl, butyl, pentyl, hexyl, heptyl, octyl, nonyl, decyl, eicosyl, triacontyl, tetracontyl, pentacontyl, hexylcontyl and the like; aryl, for example, mono- and dinuclear aryl such as phenyl, naphthyl and the like; or an unsaturated radical containing one or more ethylenic groups [>C=C<] such as ethenyl, 1-methylethenyl, 3-butenyl-1,3-diyl, 2-propenyl-1,2- diyl, carboxy lower alkenyl, such as 3-carboxy-2-propenyl and the like, lower alkoxy carbonyl lower alkenyl such as 3-methoxycarbonyl-2-propenyl and the like; tri-lower alkyleneamino such as trimethyleneamino, triethyleneamino and the like; $R^1$ is hydrogen, lower alkyl of from 1–5 carbon atoms such as methyl, ethyl, n-propyl, n-butyl, sec-butyl, tert-butyl, pentyl and the like or hydroxy lower alkyl of from 1–5 carbon atoms such as hydroxyethyl, 3-hydroxypropyl, 2-hydroxypropyl, 4-hydroxybutyl, 3-hydroxybutyl, 2-hydroxy-2-methylpropyl, 5-hydroxypentyl, 4-hydroxypentyl, 3-hydroxypentyl, 2-hydroxypentyl and the isomers of pentyl; n is an integer having a value of 1 to 10, preferably 1 or 2, and n' is an integer of 0 to 2 or when n' is 0, a polymer or copolymer (i.e., n has a value greater than 1 preferably 2–10) formed from the β-hydroxy-alkylamide when A is an unsaturated radical.

Examples of preferred compounds fall within formula I where A is an alkylene group, preferably ($C_2$–$C_8$)alkylene.

Examples of the most preferred compounds fall within the formula:

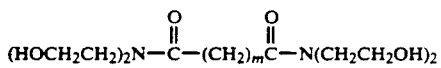

wherein m is 0–10, preferably 2–8.

Specific examples falling within Formula Ib are bis[N,N-di(β-hydroxyethyl)]adipamide, bis[N,N-di(β-hydroxyethyl)]azelamide.

The β-hydroxyalkylamides (I, supra) may be prepared by aminolysis of an ester of Formula II (infra) with an amine of Formula III (infra) at a temperature in the range of from about ambient up to about 200° C. The aminolysis reaction is typically carried out using a molar ratio of amine to ester of 2.0/1, preferably 1.95–2.05/1, and most preferably 1.98–2.02/1. In addition, the water content of the aminolysis reactants is typically controlled to less than 0.5% moisture and preferably to less than 0.1% moisture in order to maintain the activity of any basic catalyst that may be used and to minimize unwanted hydrolysis of ester reactants. Control of reactant mole ratio and moisture level is typically practiced in aminolysis reactions in order to maximize product yield and purity. Optionally, a basic catalyst may be employed, for example, potassium methoxide or butoxide; quaternary ammonium alkoxides, such as tetramethylammonium methoxide and the like; or alkali metal or quaternary ammonium hydroxides at an amount in the range of from 0.1 to 1.0 wt. % based on the weight of the ester. The reaction is preferably conducted at elevated temperatures. The following equation illustrates this process:

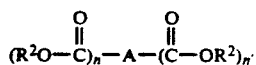 II

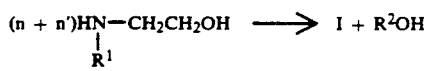 III $$\longrightarrow I + R^2OH$$

wherein A, $R^1$, n and n' are as defined above and $R^2$ is lower alkyl of from 1–5 carbon atoms such as methyl, ethyl, propyl, n-butyl, tert-butyl, pentyl and the like.

The esters (II, supra) employed above are either known compounds or are prepared by esterifying the corresponding acid by standard esterifying procedures well-known to those skilled in the art. Among the preferred acids and mixtures thereof which can be employed are oxalic, malonic, succinic, glutaric, adipic, pimelic, suberic, azelaic, sebacic, 1,4-cyclohexane dicarboxylic and the like and alkyl derivatives thereof. Also, there may be employed dimer and trimer acids and mixtures thereof prepared by the polymerization of $C_{18}$ fatty acids such as a dimer acid with 2 carboxy groups, 36 carbon atoms and an approximate molecular weight of 565 of a trimer acid with 3 carboxy groups, 54 carbon atoms and an approximate molecular weight of 850.

Some representative examples of the amines which can be employed include 2-aminoethanol; 2-methylaminoethanol; 2-n-butylaminoethanol.

The crude reaction mixture from the aminolysis (reaction of II with III) is maintained at a temperature of 25°–200° C., preferably 80°–115° C., until a thick slurry is formed. By manipulating the temperature, the mixture is then maintained in slurry form during subsequent isolation steps (flaking, spray drying, casting, and the like). It is important that the maximum "thickness" of the slurry be maintained during the final isolation steps, and it is important to maintain good agitation of the slurry during these steps. We have found that maximizing slurry "thickness" (as measured by bulk viscosity of the fluid mixture) unexpectedly maximizes the purity of the final product hydroxyamide.

Control of in-process viscosity may be attained by continuous monitoring via on-line viscometer instrumentation. In large-scale reactors (300-gallons and larger) relative viscosity changes have been found to be most useful; typical changes in bulk viscosity upon formation of a slurry range from 2 to 200 times the bulk viscosity of the reaction mixture prior to formation of the slurry. Specific viscosities of 300–2,500 cps (Brookfield Viscometer, 100 rpm, 34 sec$^{-1}$) are suitable for producing high purity hydroxyamides, with 600–2,000 cps being a preferred viscosity range, when lab-scale equipment, e.g., 1-liter reactor, is used. In-process pressure is not critical to the use of the invention and vacuum or elevated pressures may be used to satisfy individual process requirements; however, it is preferable to use a slight vacuum (50–300 mm Hg) to remove residual methanol (or other alcohol byproducts) from the aminolysis reaction. Hold times may vary widely depending on the vacuum conditions and temperatures employed for the aminolysis; thereafter the temperature of the crude liquid reaction mixture is controlled in such a way to form the thick slurry. The thick slurry condition is maintained with good agitation and temperature control from about 15 minutes up to at least about 12 hours, preferably 1–3 hours, in order to achieve maximum purity of the hydroxyamide. The aminolysis may also be carried out in a solvent, in which case the solvent should be removed prior to formation of the slurry; moreover, solvent may enable the aminolysis to be conducted at lower temperatures, resulting in less byproduct formation in some cases. Practice of the process of the invention may be by batch, continuous or semicontinuous modes.

Scheme I presents an outline of the postulated chemistry of the process steps involved in the use of the invention. The reaction of dimethyladipate (DMAd) and diethanolamine (DEA) is used for illustrative purposes. The initial base-catalyzed (KOH, or other strong bases) transesterification (Equation IV) rapidly forms the theoretical diester intermediate (DE) along with methanol. DE is then believed to convert to the desired hydroxyamide (HAm) product (Equation V) or the amide-ester dimer, AED (Equation VI); the latter (in the presence of DEA) subsequently establishes an equilibrium with HAm (Equation VII). The formation of AED is a primary source of impurity in final product HAm and also the main cause of low HAm yield.

During the aminolysis reaction, all of the Scheme I components are present simultaneously in solution. As the methanol is stripped off, the HAm may begin to "crystallize" from the mixture, i.e., to form a solid in liquid (slurry), due to its lesser solubility in the reaction medium in the absence of methanol. As additional HAm crystallizes from the molten slurry mixture, the equilibrium is shifted toward HAm at the expense of DEA, DE, and AED, all of which are undesirable components in the HAm product. The crystallization of HAm is relatively slow; therefore, extended hold times tend to produce purer product and more viscous slurries. The viscosities of the slurries should be maintained as high as possible to maximize the purity and yield of the HAm, but the viscosities should not be so high that the reaction mixture completely solidifies ("sets up"), e.g., above 2,500 cps absolute viscosity at 80° C. in small-scale lab reactors.

DMAd addition. The reaction solution is then poured into an aluminum dish at 20°-25° C. to isolate the HAm product. Analytical data on the HAm products obtained by the processes of Examples 1 (invention) and 2 (prior art) are presented in Table I.

TABLE I

|  | Example 1 Present Invention | Example 2 Control |
|---|---|---|
| Physical Appearance: | free-flowing, white chalky solid | sticky, white solid |
| % Residual DEA: | 5.3 | 9.0 |
| M.P. (°C.): | 124 | 117 |

EXAMPLE 3

In a manner similar to Example 1, a mixture of diethanolamine (DEA), 129 g, and potassium t-butoxide, 2.4 g, is placed in a 500-ml glass reactor and blanketed with nitrogen. After DMAd (106 g) is added and methanol distilled off, the reaction temperature is then increased to 108°-110° C. and held for 30 minutes to slowly convert the HAm to its molten state; the temperature is then lowered to 87° C. over a period of 25 minutes at which point a thick slurry state is obtained again. Samples are withdrawn from the reactor at each stage of this

SCHEME I

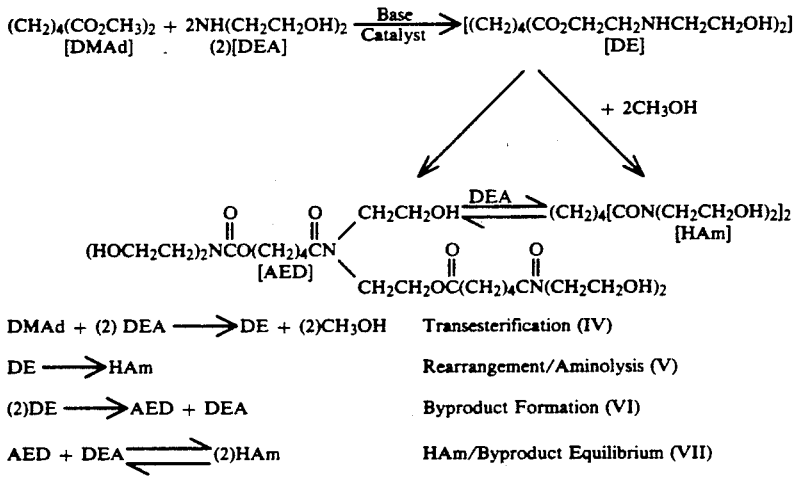

| DMAd + (2) DEA ⟶ DE + (2)CH$_3$OH | Transesterification (IV) |
|---|---|
| DE ⟶ HAm | Rearrangement/Aminolysis (V) |
| (2)DE ⟶ AED + DEA | Byproduct Formation (VI) |
| AED + DEA ⇌ (2)HAm | HAm/Byproduct Equilibrium (VII) |

EXAMPLE 1

A mixture of diethanolamine (DEA), 131 g, and potassium hydroxide (KOH), 0.5 g, is placed in a 500-ml glass reactor and blanketed with nitrogen. This mixture is heated to 100° C. under 205 mm Hg vacuum with stirring, at which point dimethyladipate (DMAd) is introduced into the mixture dropwise; the DMAd (106 g) is added over a 4 hour period during which methanol is simultaneously distilled from the reaction mixture. Within one hour after completion of the DMAd addition, the reaction mixture develops the appearance of a thick, white slurry. The slurry is maintained at 100°-103° C. for an additional 1.75 hours; the HAm product is isolated by pouring the slurry into an aluminum dish at 20°-25° C.

EXAMPLE 2 (COMPARATIVE)

In a manner similar to Example 1, the aminolysis is repeated and the reactor temperature is maintained at 93° C. such that the reaction mixture maintains its homogeneous character without forming a slurry after the process, allowed to cool and solidify to produce product HAm. Experimental conditions and analytical data obtained from on-line sampling are presented in Table 2.

TABLE 2

| Time (min) | Temp (°C.) | Operation/ Comments | % HAm | % DEA | AED/ HAm |
|---|---|---|---|---|---|
| 0 | 84 | Start DMAd addition |  |  |  |
| 30 | 79 | Reaction mixture cloudy |  |  |  |
| 50 | 84 | Formation of slurry, temp increased |  |  |  |
| 60 | 108 | DMAd addition complete |  |  |  |
| 75 | 110 | Thick slurry (A) | 90.4 | 1.7 | 0.043 |
| 90 | 109 | Thick slurry (B) | 90.8 | 1.6 | 0.044 |
| 120 | 109 | Thinner slurry (C) | 90.0 | 1.9 | 0.056 |
| 150 | 108 | Cloudy, no slurry (D) | 84.8 | 2.4 | 0.064 |
| 180 | 108 | Cloudy, no slurry (E), temp lowered | 83.1 | 3.1 | 0.085 |

TABLE 2-continued

| Time (min) | Temp (°C.) | Operation/ Comments | % HAm | % DEA | AED/ HAm |
|---|---|---|---|---|---|
| 205 | 87 | Slurry (F) | 90.0 | 1.6 | 0.042 |

HAm and AED/HAm ratios are determined by HPLC analyses. The data indicate that "slurry" conditions (samples A, B, C, and F) are conducive to high purity product (90+% HAm, <2% DEA, lower AED/HAm ratio), whereas "molten" conditions (samples D and E), representing the prior art, are conducive to low purity product (<85% HAm, >2% DEA, higher AED/HAm ratio).

I claim:

1. A process for preparing an hydroxylamide compound of the formula:

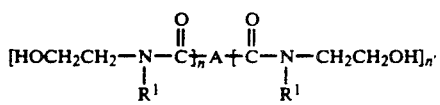

wherein A is a bond, a polyvalent organic radical or when n' is zero, A may be a hydrogen or a monovalent organic radical wherein the polyvalent or monovalent organic radical is derived from a saturated or unsaturated ($C_1$-$C_{60}$)alkyl, aryl, carboxy lower alkenyl, lower alkoxycarbonyl lower alkenyl, or tri-lower alkyleneamino; $R^1$ is hydrogen, lower alkyl or hydroxy lower alkyl; n is an integer of 1 to 10; and n' is an integer of 0 to 2; which comprises treating in the absence of a solvent a compound of the formula:

where A, n and n' are as defined above and $R^2$ is lower alkyl with a compound of the formula:

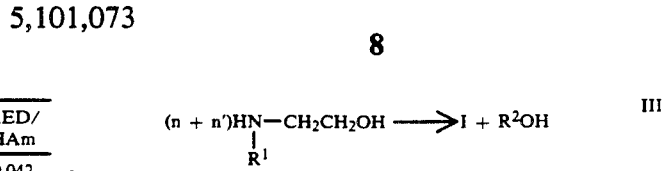

wherein $R^1$, $R^2$, n, and n' are as defined above at a temperature in the range of from ambient up to about 200° C. optionally in the presence of a catalyst and controlling the temperature to cause the hydroxyamide compound (I) to crystallize to form a slurry and maintaining the slurry by temperature control and agitation while removing byproduct $R^2OH$ for from about 0.25 to 12 hours.

2. The process of claim 1 wherein A is a bond, hydrogen, or a monovalent or polyvalent organic radical selected from a saturated or unsaturated alkyl, aryl, carboxy lower alkenyl or lower alkoxycarbonyl lower alkenyl; $R^1$ is hydrogen, lower alkyl, or hydroxy lower alkyl; n is an integer having a value of 1 or 2; and n' is an integer having a value of 0 to 2.

3. The process of claim 2 wherein the temperature control of the slurry is maintained at from about 25° to about 200° C.

4. The process of claim 2 wherein the temperature control of the slurry is maintained at from about 80° to about 115° C.

5. The process of claim 2 wherein the slurry is maintained for from about 1 to about 3 hours.

6. The process of claim 2 wherein the hydroxyamide compound is solidified by flaking, prilling, spray drying, or casting.

7. The process of claim 2 where A is ($C_2$-$C_8$)alkylene; $R^1$ is hydroxy lower alkyl and n and n' are 1.

8. The process of claim 1 wherein the byproduct $R^2OH$ is removed by distillation.

9. The process of claim 8 wherein the formula II compound is added to the formula compound III dropwise over the time period of from about 0.25 hour up to at least about 12 hours.

* * * * *